(12) United States Patent
Collin

(10) Patent No.: US 6,428,817 B1
(45) Date of Patent: Aug. 6, 2002

(54) COMPANION ANIMAL THERAPEUTIC TREAT

(76) Inventor: Peter Donald Collin, P.O. Box 172, Sunset, ME (US) 04683

( * ) Notice: Subject to any disclaimer, the term of this patent is extended or adjusted under 35 U.S.C. 154(b) by 0 days.

(21) Appl. No.: 09/743,449

(22) PCT Filed: Jul. 6, 1999

(86) PCT No.: PCT/US99/15168

§ 371 (c)(1),
(2), (4) Date: Jan. 10, 2001

(87) PCT Pub. No.: WO00/01399

PCT Pub. Date: Jan. 13, 2000

(51) Int. Cl.[7] .................. A61K 35/78; A61K 31/70; A61K 47/00
(52) U.S. Cl. ................. 424/725; 514/23; 424/439
(58) Field of Search ............................. 424/725, 439; 514/23

(56) References Cited

U.S. PATENT DOCUMENTS 3,683,076 A * 8/1972 Rovati ................... 424/180
5,681,569 A * 10/1997 Kuzncki et al. .......... 424/195.1
5,770,205 A * 6/1998 Collin .................... 424/195.1

* cited by examiner

*Primary Examiner*—Raymond Henley, III
(74) *Attorney, Agent, or Firm*—Rothwell, Figg, Ernst & Manbeck

(57) ABSTRACT

The present invention relates to a palatable dosage form of a "jerky stick" or treat for companion animals which includes sea cucumber fractions alone or in combination with glucosamine sulfate and/or glucosamine hydrochloride, and/or sea vegetables, and/or green tea; such jerky stick containing an effective amount of sea cucumber material for the inhibition or modulation of arthritic or nutritional problems in dogs, cats, and containing palatability co-factors which render the jerky stick attractive to the animal in need.

4 Claims, No Drawings

COMPANION ANIMAL THERAPEUTIC TREAT

This is a 371 of PCT/US99/15168 field Jul. 6, 1999.

FIELD OF THE INVENTION

The present invention involves the use of sea cucumber tissue fractions, in combination with kelp, and/or green tea extracts, for the inhibition of inflammation. These therapeutic fractions are incorporated with ingredients which provide palatability into a delivery system as a user-convenient and pet acceptable "jerky stick" or similar animal "treat" format.

BACKGROUND OF THE INVENTION

Dogs and other companion animals suffering from various forms of arthritis are in need of supplements which deliver active forms of anti-inflammatory agents in a palatable manner.

Glucosamine sulfate and glucosamine HCL and related products are described in various patents such as those by Henderson, et al, which teach the incorporation of glucosamines with other sulfated polysaccharides, vitamin C and manganese in products aimed at cartilage health. It is believed that glucosamine, or similar products, provide one or more of the biochemical components which make up the matrix of mammalian cartilage. Glucosamine is a chondroprotective agent which acts as a competitive inhibitor of inflammatory agents produced by the body which attack the cartilage and/or joint fluid in the joints.

Green tea extracts have been shown to be potent inhibitors of inflammation and collagen-induced arthritis in mice. See, Haqqi, et al., *Proc. Natl. Acad. Sci., USA*, 96:4524–29 (1999). The polyphenolic subfraction of green tea, known as epigallocatechin-3-gallate (EGCg), has proven to be an inhibitor of cartilage degradation in mammals. Id. In an experiment, purified EGCg, from Sigma Chemical Supply, St. Louis, Mo., was placed with bovine nasal cartilage explants at a concentration of22 $\mu$M. This mixture was cultured for 5 days in the presence or absence of the pro-inflammatory cytokine, recombinant human tumor necrosis factor alpha at 3 nM. The inhibition of both the basal and stimulated protcoglycan degradation by EGCg was measured using a calorimetric assay for sulfated glycosaminoglycans. See, Farndale, et al., *Biochem. Biophys. Acta*, 4:883 (1986). The results showed that EGCg was a potent inhibitor of cartilage breakdown at the sub-cellular level.

Jerky sticks, as are known in the dog treat industry, are often combinations of meat or fish by-products, gelatin, grains, vitamins, minerals, animal fat, preservatives such as BHT and BHA or mixed tocopherols that are mixed and extruded into various shapes, weights, and sizes which can vary widely. See, U.S. Pat. No. 5,773,076 for a general description of the art. Jerky sticks are given to pets as rewards or for added nutrition, or both.

Both extracts from the sea cucumber and from green tea are known to have beneficial therapeutic effects in mammals. These beneficial effects could not be utilized by veterinarians and others skilled in the art of animal care because they were not available in a palatable form. It is known to those skilled in the art of veterinary science that dogs and other mammals prefer palatability factors such as, fish, meat or meat by-products to enhance the attractiveness of therapeutic products and increase patient compliance.

Given the lack of a mode of delivery for these types of anti-inflammatory extracts that is both easy to administer for the caretaker and agreeable to the animal, there is a recognized need for the combination of an acceptable delivery form and the therapeutic extracts.

SUMMARY OF THE INVENTION

The present invention relates to a mode of delivery for biologically active fractions of sea cucumber and green tea. In this regard, the present invention describes a "jerky stick" or "dog bone" as is known in the art, being combined with the palatability factors of meat and meat by-products, garlic, smoke flavor or cheese, and the additional co-factors of glucosamine sulfate, glucosamine hydrochloride and/or green tea extracts or derivatives thereof for therapeutic treatment of inflammation and arthritis.

DETAILED DESCRIPTION OF THE INVENTION

The present invention addresses the problem of administration of anti-inflammatory treatments, specifically; sea cucumber products, glucosamines, kelps and green tea extracts by incorporating them into jerky treats with co-factors addressing the need to make the total product palatable to the animal in need.

The sea cucumber fraction delivery system for animals of the present invention includes the combination of glucosamines and/or kelp, and/or green tea extracts in the form, of a jerky stick, or "treat", as is popular in the dog-treat industry.

The "jerky stick" of the present invention combines certain ingredients and is made palatable by certain co-factors such as meats or flavorings known to those skilled in the art and include glucosamines or glucosamine derivatives. Sea cucumber body wall finely divided, including the epithelial layer, muscle layer and collagen layer as an ingredient in a formed dog jerky stick is also an aspect of the present invention. These total sea cucumber skin fractions are also incorporated with glucosamines described above and formed in various percentages of incorporation into jerky sticks with palatability factors such as beef, meat meal and meat by-products or other flavor-bearing compounds. A suitable range of glucosamine concentration is between 1% and 50% of the final product (by weight). These jerky sticks or manufactured "treats" are administered to dogs, cats and other animals and provide increased attractiveness to those animals in need of the therapeutic ingredients.

As used herein, the term "B1000" refers to the isolated epithelial layer of the sea cucumber, substantially free of the flower portion, muscle, collagenous tissues and viscera;

the term "T2000" refers to the isolated flower portion of the sea cucumber, substantially free of other portions of the sea cucumber body;

the term "derivative" refers to any compound, fraction or combination thereof, derived from a sea cucumber or green tea fraction that has biological activity or nutritional properties;

the term "inflammation disorder" refers to any condition or disease in a warm-blooded animal having inflammation as a symptom or proximate cause.

In one embodiment of the invention the delivery form "jerky treat" material contains the sea cucumber fractions as disclosed in U.S. Pat. No. 5,770,205. Active anti-inflammatory compositions can be obtained from sea cucumber in a variety of ways. For example, sea cucumbers can first be cleaned of muscle bands and viscera, boiled (but not salted), preferably for about ½ hour, and then dried, preferably in low-heat mechanical driers such as those employing "heat pump" technology. The dried tissue can further be ground or divided as needed for ultimate use. This process decreases the sodium content of the tissue and helps protect various active ingredients from degradation. This fraction can be formulated and used directly as an anti-inflammatory composition.

Another active fraction can be obtained from the flower portion of the sea cucumber. During the evisceration process described above, the anterior portion ("flower") of the sea cucumber is cut away from the viscera and body wall. The isolated flower is then heated, preferably for about ½ hour, dried at low temperatures (e.g. between about 140° F. and about 180° F. using conventional drying apparatus and per se known techniques). This dried fraction, designated "T2000" by the inventor, can then be ground or divided as needed for formulation and use directly as an anti-inflammatory composition.

Still another anti-inflammatory fraction can be obtained from the epithelial layer of the sea cucumber body wall. Muscle, viscera and flower are removed as described above, followed by isolation of the epithelial layer of the sea cucumber body wall from the harder collagenous layers beneath, preferably by one or more of the following means:

heating the body-wall in water at temperatures from about 140° F. to about 180° F., preferably at about 170° F., followed by mechanical separation by hand or machine (e.g., using machines known in the art as mincers or de-boners, which detect tissue density and separate harder tissues from softer tissues);

enzymatic hydrolytic separation, using, e.g., organism's own digestive tract enzymes, proteases from mammalian sources, proteases from non-mammalian sources or acidic hydrolazes, preferably Alcalase (NOVO Nordisk Bio Chem, North Carolina), the enzyme preferably being in a solution of about 1% to about 10% enzyme, most preferably in a solution of about 10% enzyme;

scouring/scrubbing or de-boning processes known to those skilled in the potato or chicken processing arts.

Heating in water, followed by mechanical separation using a de-boner is most preferred.

The epithelial fraction so obtained (designated "B1000" by the inventor) is a dark, moist, viscous, carbohydrate-rich matter. B1000 can be dried as described above, formulated and used directly as an anti-inflammatory composition.

Once produced, the B1000 and/or T2000 fractions, other sea cucumber tissues, and kelp, are incorporated into the mixture for the preparation of the "jerky treats" in amounts between 1% and 80% by weight. These therapeutic constituents are then added to the combinations of meat or fish by-products, gelatin, grains, vitamins, minerals, animal fat, preservatives such as BHT and BHA or mixed tocopherols and palatability factors such as beef, meat meal and meat by-products or other flavor-bearing compounds that are mixed and extruded into various shapes, weights, and sizes which can vary widely.

In another embodiment of the invention, green tea or green tea extracts are added to the formulation. Green tea is known to contain potent inhibitors of cartilage degradation, for example EGCg, and is a useful adjunct for treating individuals with inflammatory diseases, such as arthritis, that can lead to cartilage degradation. Green tea can be water and alcohol extracted by methods known in the art whereby the phenolic fraction is between 30% and 70%. Green tea extracts having 30%, 50%, 60% and 100% enriched polyphenolics, or specifically green tea catechins, are available commercially and are suitable for use in the present invention. Extracts are incorporated into the "jerky stick" of the present invention at percentages of weight between 1% and 80% of the total "jerky stick" delivery form. Alternatively, the pure compound EGCg can be added directly to the "jerky stick" formulation in amounts ranging up to 60% by weight or more, limited by factors such as $LD_{50}$ and the physical considerations of maintaining a palatable consistency to the product.

EXAMPLE 1

Preparation of the "Jerky Stick" with Sea Cucumber and Kelp Fractions

Jerky sticks were prepared using T2000 from the Sea Cucumber, *Cucumaria frondosa*, as described above. T2000, together with various palatability factors including, but not limited to, meat, meat by-products and "Norwegian" kelp, *Ascophylum nodosum,* were added to vitamin E, garlic, lecithin, gelatin, glucosamine (as a hydrochloride salt, although the sulfate salt or any other suitable form) and flax seeds. The T2000 was added at about 8% of the final treat product by weight. The glucosamine constituent was added at 2% of the final treat product by weight. The ingredient mix was then extruded and molded into a jerky stick shape 5 inches long, 1.25 inches wide and approximately 0.25 inches thick, with final weight of 14 grams.

EXAMPLE 2

Preparation of the "Jerky Stick" with Additional Green Tea Fractions

The jerky stick was produced as in Example 1, with the addition of a green tea extract containing 30% polyphenolics. The green tea extract, purchased from Indena USA. Seattle Wash., USA, Product 36TVD0090-"THE VERT" AQ-ATO-HF, was added to the above recipe at 2% by weight, but can be added at any percentage of the jerky stick weight between 1% and 30% (limited by palatability). This provided an effective dose of 280 milligrams of the green tea extract to the jerky product. It is contemplated that the epigallocatechin3-gallate (EGCg) is absorbed systemically in mammals, and is effective in inhibiting degradation of cartilage in arthritic joints. In addition, EGCg is thought to provide added synergy to the anti-inflammatory activity of the sea cucumber and the sea cucumber plus glucosamine compounds.

EXAMPLE 3

Effectiveness and Palatability of the "Jerky Stick" in Arthritic Dogs

Jerky sticks with added green tea extracts were administered to 4 dogs of unknown breeds at Westside Animal Clinic in Richmond, Ind. and were found to be palatable.

Further, six arthritic dogs in various conditions of lameness were administered jerky sticks as prepared in Example 1. After two weeks of administration at one stick per day per 50 pounds of weight, these dogs showed increased mobility as determined by both their owners and veterinarians. In every instance, palatability was not a problem in administration of the jerky.

It should be understood that the examples and embodiments described herein are for illustrative purposes only and that various modifications or changes in light thereof will be suggested to persons of ordinary skill in the art and are to be included within the spirit and purview of this application and the scope of the appended claims.

What is claimed is:

1. A dosage form for administering therapeutic agents to animals in need thereof comprising fractions of sea cucumber in percentages of incorporation between 1 and 80% by weight, glucosamine HCL or glucosamine sulfate in percentages of incorporation between 1 and 50% by weight and one or more palatability factors in amounts sufficient to successfully render the composition of matter palatable to target animals, said dosage form being of a weight between 1 gram and 30 grams.

2. A method of delivery of sea cucumber fractions to animals by the administration of a jerky treat dosage form which contains an effective amount of sea cucumber fractions.

3. A method to provide increased mobility and relieve nutritional and arthritic or inflammatory symptoms in an animal in need of same by the combining of glucosamine or salts thereof with sea cucumber fractions at percentages of each compound between 1% and 90% to the total.

4. A composition of matter of claim 1, additionally comprising green tea extract in an effective amount to inhibit inflammation in a mammal in need of same.

* * * * *